United States Patent [19]

Haag et al.

[11] 4,323,698

[45] Apr. 6, 1982

[54] RESIN-METAL COMPOUND COMPLEX FOR CATALYZING CHEMICAL REACTIONS

[75] Inventors: Werner O. Haag, Lawrenceville; Darrell D. Whitehurst, Titusville, both of N.J.

[73] Assignee: Mobil Oil Corporation, New York, N.Y.

[21] Appl. No.: 113,897

[22] Filed: Jan. 21, 1980

Related U.S. Application Data

[60] Division of Ser. No. 965,829, Dec. 4, 1978, Pat. No. 4,211,880, which is a division of Ser. No. 858,228, Dec. 7, 1977, Pat. No. 4,145,486, which is a continuation of Ser. No. 501,429, Aug. 29, 1974, Pat. No. 4,111,856, which is a continuation of Ser. No. 306,782, Nov. 15, 1972, which is a continuation-in-part of Ser. No. 860,807, Sep. 24, 1978, abandoned, which is a continuation-in-part of Ser. No. 672,010, Oct. 2, 1967, abandoned.

[51] Int. Cl.³ .................. C07C 67/36; C07C 51/12; C07C 5/03; C07C 45/49
[52] U.S. Cl. .................. 560/233; 252/431 R; 260/544 A; 260/544 Y; 560/234; 560/241; 560/243; 560/245; 562/607; 568/451; 568/456; 585/250; 585/275; 585/276; 585/277; 585/369; 585/370; 585/378; 585/507; 585/832
[58] Field of Search .................. 260/544 A, 544 Y; 252/431 R; 585/250, 275, 276, 369, 277, 370, 832, 378, 507; 560/233, 234, 241, 243, 245; 562/607; 568/451, 456

[56] References Cited

U.S. PATENT DOCUMENTS

| 2,565,461 | 8/1951 | Bliss et al. | 260/544 A |
|---|---|---|---|
| 2,683,124 | 7/1954 | D'Alelio | 252/431 |
| 2,779,781 | 1/1957 | Copelin et al. | 252/431 |
| 3,097,237 | 7/1963 | Sauer | 260/544 A |
| 3,280,096 | 10/1966 | MacKennis | 252/431 |
| 3,288,725 | 11/1966 | Aftandilian | 252/447 |
| 3,338,961 | 8/1967 | Closson et al. | 260/544 A |
| 3,417,066 | 12/1968 | Corte et al. | 252/431 |
| 3,442,924 | 5/1969 | Imura et al. | 252/431 |
| 3,442,954 | 5/1969 | Crocker et al. | 560/243 |
| 3,450,730 | 6/1969 | Scheben et al. | 260/544 A |
| 4,111,856 | 9/1978 | Haag et al. | 521/30 |
| 4,145,486 | 3/1979 | Haag et al. | 521/31 |
| 4,211,880 | 7/1980 | Haag et al. | 560/243 |

*Primary Examiner*—Natalie Trousof
*Assistant Examiner*—Vera C. Clarke
*Attorney, Agent, or Firm*—Charles A. Huggett; Michael G. Gilman; Charles J. Speciale

[57] ABSTRACT

This specification discloses an insoluble resin-metal compound complex, the method for its preparation, and its use in carrying out a catalyzed reaction. The complex is a weak base anion exchange resin which has been contacted with a solution of a coordination compound having at least two ligands connected to at least one central metal atom to bond chemically the resin to the metal atom by replacement of at least one of the ligands of the coordination compound by a functional group of the weak base anion exchange resin. The complex can be used as a catalyst for hydrogenation, carbon monoxide insertion, polymerization, isomerization, vinyl ester exchange, and ethylene oxidation reactions, among others.

10 Claims, No Drawings

RESIN-METAL COMPOUND COMPLEX FOR CATALYZING CHEMICAL REACTIONS

CROSS REFERENCE TO RELATED APPLICATIONS

This application is a division of copending application Ser. No. 965,829 filed Dec. 4, 1978, now U.S. Pat. No. 4,211,880, which in turn is a division of application Ser. No. 858,228, filed Dec. 7, 1977, now U.S. Pat. No. 4,145,486, which is a continuation of application Ser. No. 501,429, now U.S. Pat. No. 4,111,856, filed Aug. 29, 1974, which is a continuation of application Ser. No. 306,782, filed Nov. 15, 1972. Application Ser. No. 306,782 is a continuation in part of our copending application Ser. No. 860,807, filed Sept. 24, 1969, and now abandoned. Application Ser. No. 860,807 is a continuation-in-part of our application Ser. No. 672,010, filed Oct. 2, 1967. This latter application was copending with application Ser. No. 860,807 but is now abandoned.

BACKGROUND OF THE INVENTION

1. Field of the Invention

This invention relates to insoluble resin-metal compound complexes.

2. Description of the Prior Art

U.S. Pat. No. 2,683,124 discloses anion-exchange resins comprising water-insoluble, infusible resins containing a pyridyl nucleus, such as prepared from vinyl pyridines and vinyl quinolines and their alkyl and alkenyl derivatives by cross-linking with cyclic diene compounds.

U.S. Pat. No. 2,779,781 discloses the use of an insoluble quaternary ammonium anion-exchange resin for the cyanidation of 1,4-dichlorobutane.

Herber et al., in the Journal of the American Chemical Society, Vol. 76 (1954), pages 987-991, disclose the anion-exchange behavior of anionic solutions of cobalt, copper, zinc, and gallium on a strongly basic resin, Dowex-1, a quaternary ammonium polystyrene-divinyl benzene copolymer.

Moore et al., in the Journal of the American Chemical Society, Vol. 72 (1950), pages 5792-3, disclose the adsorption of iron from a relatively concentrated hydrochloric acid solution on Dowex-1 by anion exchange.

Nachod et al., in Ion Exchange Technology (1956) published by Academic Press Inc., New York, N.Y., pages 292-297, disclose a tabulation of hydrometallurgical ion exchange applications with sulfonated and carboxylic cation exchange resins and weak and strong base anion exchange resins.

U.S. Pat. No. 3,280,096 discloses a polymerization catalyst comprising the reaction product of hydroxyl groups on the surface of an inorganic solid and an organometallic compound of a Group IVb metal.

U.S. Pat. No. 3,288,725 discloses a hydrogenation catalyst produced by reacting hydroxyl groups on the surface of a finely divided inorganic solid and an organometallic compound of a Group VIII metal.

U.S. Pat. No. 3,417,066 discloses a procedure for chloromethylating and crosslinking high molecular weight aromatic polymers and their conversion to ion-exchange resins by treatment with amines, polyamines, aminocarboxylic acids, aminosulfonic acids, or aminophosphonic acids, or by oxidation.

U.S. Pat. No. 3,442,924 discloses a process for the preparation of mixed alkyl lead compounds employing as catalyst a metal salt of a strongly acid cationic exchange resin obtained by reacting a salt of the metal with the resin.

U.S. Pat. No. 3,442,954 discloses an oxidation catalyst comprising a macroreticular resin containing sulfonic acid groups, the hydrogen ion of which has been exchanged by a metal ion by loading the resin with an ionic form of the metal.

SUMMARY OF THE INVENTION

In accordance with an aspect of the invention, there is provided an insoluble resin-metal compound complex and the method of making it comprising contacting an insoluble weak base anion exchange resin with a solution of a coordination compound having at least two ligands connected to at least one central metal atom, the metal being selected from the group consisting of platinum, palladium, rhodium, ruthenium, osmium, iridium, gold, cadmium, titanium, zirconium, hafnium, vanadium, chromium, molybdenum, tungsten, manganese, rhenium, iron, cobalt, nickel, copper, zinc, silver, and mercury, at a temperature below the decomposition temperature of the weak base anion exchange resin and the coordination compound for a time sufficient to bond chemically the weak base anion exchange resin to the metal atom of the coordination compound by replacement of at least one ligand of the coordination compound by a functional group of the weak base anion exchange resin.

In accordance with another aspect of the invention, there is provided a method of carrying out a metal compound-catalyzed reaction employing as a catalyst the insoluble resin-metal compound complex.

DESCRIPTION OF THE SPECIFIC EMBODIMENTS

The weak base anion exchange resin is a resin, exemplified by a styrene-divinylbenzene copolymer, having attached thereto a non-ionic functional group or ligand exemplified by a primary amine. The weak base anion exchange resin is not in itself an anion exchange resin since it does not have attached thereto an ionic functional group or ligand. Thus, the weak base anion exchange resin does not have attached thereto an ion which can be exchanged for another ion.

Weak base anion exchange resins are characterized by the fact that they possess essentially no ion exchange properties at pH levels greater than pH 7 as above this pH they contain no ionic groups. They are composed of polymers containing primary, secondary, or tertiary amines, phosphines, arsines, stibines, thiols, or sulfides. These materials are to be distinguished from strong base anion exchange resins which consist of polymers containing quaternary ammonium phosphonium or arsonium salts or tertiary sulfonium salts. Strong base anion exchange resins have the capacity to undergo ion exchange independent of the pH of the medium by virtue of their intrinsic ion character. Further definition of strong and weak base ion exchange resins along with their preparation and properties are described in F. Helfferich "Ion Exchange", McGraw Hill Book Co., New York, N.Y., 1962, pp. 16, 47–58, 78, 138–40, and in "Dowex-Ion Exchange", the Dow Chemical Co., Midland, Mich., 1958. Due to their ability in strong acid solutions to form ionic compounds with exchangeable anions, the weak base resins are commonly referred to in the art as "anion exchange resins" and specifically as "weak base anion exchange resins". When the weak base anion exchange resin is treated with metal compounds in the absence of strong acids, a ligand exchange can occur; for example, in the reaction

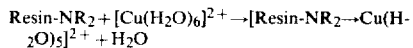

a ligand on copper, water, is replaced by a functional group of the resin, $-NR_2$, acting as a ligand or Lewis base. No anion exchange has occurred; the metal is attached to the ligand by covalent or coordinative bonds rather than by ionic bonds. When used in this way, the anion exchange resins would be more appropriately termed "coordination resins". It is this ability of the weak base anion exchange resins to form coordinative bonds to metals that is utilized in the present invention.

A simple test may be employed to differentiate between a weak base and a strong base anion exchange resin. A strong base anion exchange resin has a salt splitting capacity that exceeds 80% of the total capacity. A resin having only weak base anion exchange sites has a salt splitting capacity of less than 20% and most often less than 5% of the total capacity. The total capacity is the number of basic or functional groups, such as amines, phosphines, etc., as determined by chemical analysis and expressed in milliequivalents per gram. It may also be determined by simple titration procedures, as described in Helfferich (loc. cit.), pages 91 and 92. The salt splitting capacity is determined as follows: the resin is first treated with an excess of an aqueous solution of 0.1 N sodium hydroxide preferably in a column operation. The resin is then washed with distilled water until the washings are essentially neutral (pH 6–8.5). Thereafter, the resin is washed with an aqueous solution of an ionic salt such as sodium chloride until the effluent is essentially neutral (pH 6–8.5). The combined washings are then titrated with standard acid to determine the alkalinity of the effluent. The alkalinity, expressed in milliequivalents of base per gram resin, is equal to the salt splitting capacity of the resin.

The resin employed as the resin portion of the weak base anion exchange resin must be insoluble. By "insoluble" we mean insoluble at temperatures below the decomposition temperature of the resin in solvents such as water, alcohols, ketones, ethers, esters, acetic acid, in saturated, unsaturated or cyclic aliphatic and aromatic hydrocarbons, and in the same hydrocarbons having substituents consisting of or containing oxygen, sulfur, nitrogen, or the halides. The resin must also be porous under reaction conditions and be inert to the catalytic reaction for which it is to be used.

Suitable resins include: insoluble organic polymers, as are obtained by addition-polymerization or poly-condensation of suitable monomers; insolubilization when needed is achieved by chemical crosslinking, by radiation or by thermosetting. Examples of polymers are polystyrene, polyethylene, polyvinyl chloride, polyvinyl acetate, polyethylene imine and other polyalkylene imines, polyvinyl pyridine, polyacrylonitrile, polyacrylates, saran, and teflon.

Suitable crosslinking agents, particularly for polyolefins, are divinylbenzene, butadiene, diallyl maleate, diallyl phthalate, glycol dimethacrylate, and other di- or triolefins.

A particularly useful resin is a commercially available copolymer of styrene and divinylbenzene. Condensation polymers include phenol-formaldehyde resins, urea-formaldehyde resins, alkyd resins (reaction products of polyhydric alcohols and polybasic acids), polyesters, such as dacron and polyamides. Also suitable are polyamines, polyethers such as polyphenyl oxide, polystyrene oxide or polypropylene oxide, polysulfides such as polyphenyl sulfide, and polysulfones such as polyphenyl sulfone. Mixtures of copolymers are also suitable. Celluloses are also included although they are not normally considered resins.

The resin matrix of the weak base anion exchange resin contains chemically bonded thereto a basic, non-ionic functional group. The functional groups include primary, secondary, or tertiary amine groups. These may be aliphatic, aromatic, heterocyclic or cycloalkane amine groups. They may also be diamine, triamine, or alkanolamine groups. The amines may include alpha, alpha'-dipyridyl, guanidine, and dicyandiamidine groups. Other nitrogen-containing basic, non-ionic functional groups include nitrile, cyanate, isocyanate, thiocyanate, isothiocyanate, and isocyanide groups. Pyridine groups may also be employed.

Resins containing bonded thereto, as basic, non-ionic functional groups, phosphine, arsine, stibine, or sulfide groups may also be employed. These groups may be either alone or with other groups also present. The phosphine, arsine, and stibine groups can be primary, secondary, or tertiary. Of these, the tertiary groups are preferred. The substituents on the phosphorous, arsenic, or antimony atoms may be, for example, alkyl or aryl groups or halogen atoms and other groups and atoms. Included among the sulfide groups are primary sulfides, such as mercaptans (thiols) and thiophenols; secondary sulfides such as dialkyl sulfides, dialkyl disulfides, and dialkyl trisulfides, aromatic heterocyclics such as thiophene and substituted thiophenes such as benzothiophene; and thiazole.

Other useful sulfide functional groups wherein the resin matrix has replaced one or more of the hydrogen atoms of the sulfide compound are:
1,2-Dimercapto-4-methylbenzene
Sodium cis-1,2-dicyanoethylene-1,2-dithiolate (disodium maleonitrile dithiolate)
2-Mercaptoethylamine (HCI)
o-Methylthioaniline
Di-t-butylsulfide
Diphenylsulfide
Di-butyl-disulfide
Cystine
Triphenylphosphine sulfide
Thio acetone
Thiophenol
Isopropyl mercaptan
o-Phenylane dimercaptan
2,4-dithiopentane
Dithiooxamide Illustrative useful phosphine functional groups where the resin matrix has replaced one or more of the hydrogen atoms in the phosphine compound are:
Tri-i-propylphosphine
Tris(di-i-propylamino)phosphine
Dicyclohexylphenylphosphine
Tris(dicyclohexylamino)phosphine
Tris(diethylamino)phosphine
Di-t-butylbenzylphosphine
Di-t-butyl-n-propylphosphine
Chlorodi-t-butylphosphine
Tri-i-butylphosphine Di-n-butylphenylphosphine
1-Ethyl-3,5,8-trioxa-4-phosphabicyclo(2,2,2)octane
Di-t-butylphenylphosphine
Tri-i-propylphosphite
Trans-Bis(1,2-diphenylphosphino) ethylene
Bis(diphenylphosphino)methane
Cyclohexyldiphenylphosphine
Dicyclohexylphenylphosphine
Dimethylphenylphosphine
Ethyldichlorophosphine
Methyldiphenylphosphine
Tetramethylbiphosphine
p-Tolyldiphenylphosphine
Tri-iso-butylphosphine
Tricyclohexylphosphine
Triethylphosphine
Triphenylphosphine
Tri-m-tolylphosphine
Tris(dimethylamino)phosphine
Tris(-p-methoxyphenyl) phosphine
Tri-n-butylphosphite
Triethylphosphite
Triphenylphosphite
Diphenylethoxyphosphine
Phenyldi-n-butoxyphosphine
Phenyldimethoxyphosphine
Bis(1,2-diphenylphosphino)ethane
Ethylenebis(diphenylphosphine
CIS-Bis(1,2-diphenylphosphine ethylene
t-Butyldichlorophosphine
Di-t-butylchlorophosphine
Diethylphenylphosphine
Diphenylphosphine
Ethyldiphenylphosphine
Phenylphosphine
Tetraphenylbiphosphine
Triallylphosphine
Tri-n-butylphosphine
Tri-2-ethylhexylphosphine
Trimethylphosphine
Tri-n-propylphosphine
Tri-o-tolylphosphine
Tri-p-tolylphosphine
1,1,1-Tris(diphenylphosphinomethyl)phosphine
Vinyldiphenylphosphine
Tri-p-chlorophenylphosphite
Trimethylphosphite
Diphenyl-n-butoxyphosphine
Diphenylmethoxyphosphine
Phenyldiethoxyphosphine Illustrative useful arsine functional groups where the resin matrix has replaced one or more of the hydrogen atoms in the arsine compound are:
Bis(1,2-diphenylarsino)ethane
Bis(diphenylarsino)methane
Dimethylarsine
o-Phenylenebis(dimethylarsine)DIARS
Triethylarsine
Triphenylarsine
Tri-p-tolylarsine Illustrative useful stibine functional groups are those in which antimony is replaced for arsenic in the above-mentioned arsine functional groups.

The weak base anion exchange resins are generally made by subjecting to appropriate chemical treatment a desired resin. For example, a styrene-divinylbenzene copolymer may be converted to an amine-type weak base anion exchange resin by first chloromethylating it and subsequently reacting it with a desired amine. Alternatively, the weak base anion exchange resin may be made by reacting all ingredients together. Thus, a weak base anion exchange resin of phenylenediamine type can be prepared by reacting phenylenediamine with formaldehyde.

The weak base anion exchange resins may be produced by successive chemical reactions or by direct copolymerization. When the weak base anion resin is to be produced by successive chemical reactions, the following sequence, for example, may be employed: first, a polystyrene-divinylbenzene copolymer is chloromethylated and the product is then treated with a metal phosphide. The arsine and stibine group-containing resins can be made in the same way. If the metal phosphide is a substituted phosphide, the correspondingly substituted weak base anion resin is obtained.

Alternatively, a resin containing sodium or lithium directly attached to the resin portion thereof, e.g., a resin containing phenylsodium or phenyllithium groups, preferably the latter, can be reacted with a halophosphine, e.g., a chlorophosphine such as diphenyl chlorophosphine. Alternatively again, a resin can be directly chlorophosphinated by the method described on page 39 of "Ion Exchange" by Helfferich, above, using a mixture of aluminum chloride and phosphorous trichloride.

The sulfide resins can be produced by the method described on page 46, 554, and 555 of "Ion Exchange" by Helfferich, above. The hydrosulfuryl groups can be converted to the alkylsulfuryl groups by first converting to the sodium form (—SNa) and then treating with the appropriate alkyl halide.

It should be understood that these methods of preparation are purely exemplary and other methods will be known or apparent to those skilled in the art.

For preparation of the insoluble resin-metal compound complex, a solution of soluble coordination compound having at least two ligands connected to at least one central metal atom is contacted with the insoluble weak base anion exchange resin. Upon contacting of the coordination compound with the anion exchange resin, the two react, with the functional group of the resin replacing one or more of the ligands of the coordination compound thereby chemically bonding the coordination compound to the resin through at least one bond which joins the central metal atom to a functional group.

By "coordination compound", we mean a complex compound whose molecular structure contains a central atom bonded to other atoms by coordinate covalent bonds. These are bonds based on a shared pair of electrons both of which come from a single atom or ion. By "soluble", we mean soluble in solvents such as water, alcohols, ketones, ethers, esters, acetic acid, in saturated, unsaturated or cyclic aliphatic or aromatic hydrocarbons or in the same hydrocarbons having substituents consisting of or containing oxygen, sulfur, nitrogen, or the halides.

The ligands of the soluble coordination compound may be ionic, neutral or mixed ligands. Anionic ligands include chloride, bromide, iodide, cyanide, nitrate, acetate, sulfide, and trichlorostannite ligands. Neutral ligands include water, ammonia, phosphine, carbon monoxide, olefin, and diolefin ligands.

The central metal atom of the soluble coordination compound may be platinum, palladium, rhodium, ruthenium, osmium, iridium, gold, cadmium, titanium, zirconium, hafnium, vanadium, chromium, molybdenum, tungsten, manganese, rhenium, iron, cobalt, nickel, copper, zinc, silver, or mercury. Preferably, the central metal atom is a metal of the platinum series, namely, platinum, palladium, rhodium, ruthenium, osmium, and iridium. Usually, the soluble coordination compound will have one central metal atom. However, it may have two central metal atoms, either the same or different.

Examples of suitable coordination compounds are potassium tetrachloropallidite, chloroplatinic acid, rhodium trichloride trihydrate, dichlorobis(triphenylphosphine)palladium(II), dichlorotetrakis-(triphenylphosphine)ruthenium(II), chlorobis(triphenylphosphine)rhodium(I), tricarbonylbis(triphenylphosphine)ruthenium(O), iodocarbonylbis(triphenylphosphine)iridium(I), potassium tetranitroplatinate(II), potassium tetrahydroxoaurate(III), sodium oxotetrafluorochromate, tetra(pyridine)platinum(II)tetrabromoplatinate, tetraamminepalladium(II)chloride, di-mu-chlorodichlorobis(-triethylarsine)diplatinum(II), di-mu-thiocyanatodithi-ocyanatobis(tripropylphosphine)diplatinum(II), and potassium trichloro(trichlorostannato)platinite(II).

The solution of the soluble coordination compound and the insoluble weak base anion exchange resin are contacted at a temperature and for a time to effect bonding of a desired amount of the coordination compound to the resin. The temperature may range between room temperature to just below the decomposition temperature of either the coordination compound or the resin. Preferably, temperatures between room temperature and the boiling point of the solvent for the coordination compound are employed. The rate at which the coordination compound reacts with the resin depends, of course, on the temperature, the rate increasing with temperature. The time of contact may range from a fraction of an hour, say one-quarter of an hour, to several hours, say twelve hours, or even one or more days, say three days. The reaction of the coordination compound with the resin, which is a strong one, takes place initially at the outer surface of the resin particle and may gradually progress inward. The reaction can, of course, be stopped at any desired time to give resin particles having varying amounts of coordination compound bonded thereto, the amounts ranging from a shell of varying thickness to complete penetration of the particle. By "shell" is meant the more exterior layer or portion of the particle which has reacted with the coordination compound. With increase in the time of reaction, a greater degree of penetration is obtained. The time of reaction will therefore depend upon the degree of penetration and the size of the particle.

The complex may comprise 0.01 to 50%, preferably 1 to 10%, by weight of metal; 0 to 60%, preferably 0.1 to 25%, and more preferably, 2 to 10%, by weight of ligand; and about 39 to 99.9% by weight of resin. The sum of the amount of the ligand and metal preferably should not exceed 61%.

The production of an insoluble resin-metal compound complex may be illustrated employing, as a soluble coordination compound having anionic ligands, potassium tetrachloropalladite, $K_2PdCl_4$, and, as an insoluble weak base anion exchange resin, commercially available under the trade name of Amberlyst-A21, a macroreticulate styrene-divinylbenzene copolymer containing dimethylaminomethyl groups. The coordination compound is dissolved in water and then mixed with the resin. The coordination compound reacts with the resin according to the following equation:

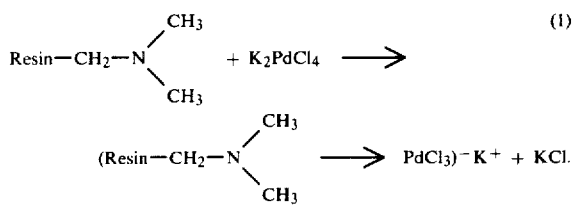

The $K^+$ is not chemically bonded to the Pd. The complex of equation (1) may then react as follows:

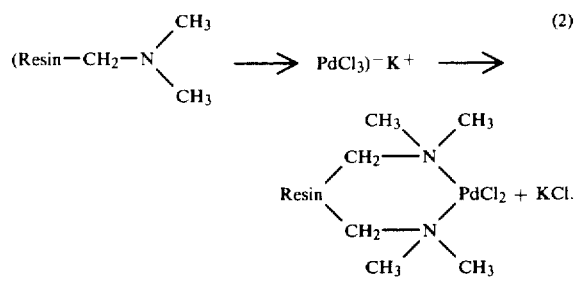

In the insoluble resin-metal compound complex of equation (2), the "ligand" is Cl, the "metal" is Pd, and the "resin" is the moiety

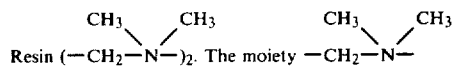

is a functional group attached to the resin. An insoluble resin-metal compound complex having 0% ligand may be illustrated by the formula:

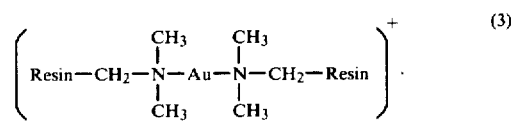

It may be made by reacting Amberlyst-A21 with gold nitrate, $AuNO_3$. However, it may have $NO_3$ ion present although not chemically bonded to the Au.

The insoluble resin-metal compound complexes may be seen to comprise an insoluble weak base anion exchange resin containing basic functional groups and chemically bonded to some of the functional groups are metal atoms, the metals having been set forth hereinabove. The bonding occurs as a result of ligand exchange, the functional group of the resin replacing one or more of the ligands of the coordination compound. The metal atoms preferably have chemically bonded thereto at least one ligand, the ligands also having been set forth hereinabove. For example, the insoluble metal compound complex set forth in equation (2) has two Cl ligands connected to the Pd atom and also two functional groups. Further, it could have one Cl ligand and three functional groups, or, as in the complex of equation (1), three Cl ligands and one functional group. In formula (3), the metal atom has only functional groups, of which there are two, attached to it. On the other hand, the insoluble metal compound complexes may have a total of three, five, six, seven, or eight ligands and functional groups. At least one functional group must be present.

The insoluble resin-metal compound complex is further characterized by its quantitative composition as set forth above.

As mentioned, the chemical bonding of the metal atoms to the functional groups in the complex is the result of ligand exchange. This bonding by ligand exchange is to be distinguished from bonding by ion exchange. Where the bonding is by ligand exchange, the metal atom cannot be removed from the complex by an ion exchange reaction. On the other hand, it may be removed by reaction of the complex with another coordinating ligand. However, where the bonding is by ion exchange, the metal atom can be removed from the complex by reaction of the complex with a solution of an ionic compound. To test whether bonding is by ligand exchange or ion exchange, the complex can be reacted with an aqueous solution of sodium perchlorate. Sodium perchlorate always acts as an ionic compound. This is not true of other metal salts whose anions may act as coordinating ligands or as ionic compounds depending upon the reaction conditions employed. If treatment of the complex with the aqueous solution of sodium perchlorate does not result in removal of the metal atom, the bonding was by ligand exchange. For some ligand bound metal complexes, water or other solvents may act as a coordinating ligand and thus promote ligand exchange.

The insoluble resin-metal compound complexes are suitable for use as catalysts in carrying out catalyzed reactions. These reactions are those that are catalyzed by soluble compounds of the metals set forth hereinabove in homogeneous catalysis. Preferably, the insoluble resin-metal compound complexes are employed as catalysts in reactions where lower temperatures prevail, say up to 200° C. or 250° C. and preferably too in liquid phase reactions. For example, they are useful in hydrogenation reactions involving compounds having carbon-to-carbon unsaturation, as in the conversion of acetylenes, olefins, and diolefins, using complexes containing compounds of platinum, palladium, ruthenium, rhodium, and other metals. For carrying out catalytic reactions generally, complexes containing as the central metal atom any of the metals described in the preceding paragraphs are of use.

Other catalytic reactions in which the resin-metal compound complexes are of value include carbon monoxide-insertion reactions, double bond isomerizations, vinyl ester interchange reactions, and olefin oxidations, e.g., ethylene oxidation. Other reactions include olefin hydroformylation, comprising the reaction of an olefin with carbon monoxide and hydrogen in the presence of complexes containing nickel, cobalt, or rhodium carbonyl moieties; olefin dimerization and polymerization in the presence of nickel or rhodium chloride-containing complexes; olefin hydrocarboxylation, hydroesterification, and hydrocyanation in the presence of complexes containing a metal carbonyl moiety, or metal hydrocarbonyl moiety, or metal phosphine-substituted carbonyl moiety; hydroquinone synthesis from acetylenes, carbon monoxide, and water, or the cyclooligomerization of acetylene to benzene and the like, the cyclooligomerization of butadiene to cyclooctadiene, or the carbonylation of acetylenes and olefins to acids. Also, acetylenes may be hydrated over ruthenium chloride-containing complexes. It will be apparent that many of these reactions involve the conversion of unsaturated compounds, particularly of unsaturated hydrocarbons like olefins and acetylenes. Referring again to ethylene oxidation, this reaction may be run in several ways; thus, ethylene may be oxidized in aqueous solution to produce acetaldehyde, or it may be oxidized in methanol solution to give vinyl methyl ether, or in acetic acid solution to produce vinyl acetate.

In view of the fact that the complex may contain some functional groups, i.e., basic groups, as well as metal compound groups, it follows that the complex may be a dual functional catalyst containing two types of sites, basic sites and metal compound sites. It is thus useful to catalyze polystep catalytic organic reactions at low temperature and in the liquid phase. In such a reaction, one type of catalytic site catalyzes a reaction step different from that catalyzed by another type of site. The different types of sites are separated by distances of the order of molecular dimensions.

Although low temperature liquid phase reactions are preferred, it will be appreciated that many low temperature reactions involve gaseous reactants and may be carried out in the gas phase, and the complexes can be applicable in these reactions. In some reactions, both liquid and gaseous reactants take part and are suitably catalyzed by the complexes. In all reactions, ease of catalyst separation by conventional operations of filtration, decantation, or centrifugation is a characteristic, whether the products and/or reactants are liquid or gaseous. The reactions may be carried out in conventional fixed bed flow reactors, or in continuously stirred flow reactors, or in batch reactors. Pressure may range to 300 atmospheres or more, and reaction times from less than one minute to several hours.

The insoluble resin-metal compound complexes may, if desired, be converted to other materials useful as catalysts by relatively simple additional steps. In one case, the complex illustrated in equation (2) was treated with an aqueous stannous chloride solution to form a complex having palladium-tin bonds. The reaction may be illustrated as follows:

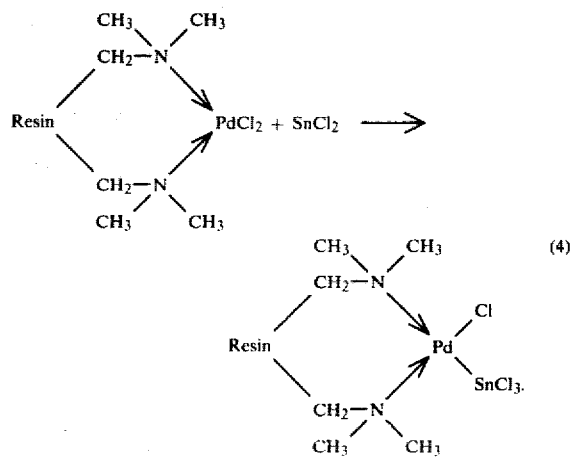

As shown, it is believed that the stannous chloride replaces a Cl ligand attached to palladium. The resulting complex has increased activity for catalyzing the formation of vinyl acetate from ethylene, oxygen, and acetic acid. Besides stannous chloride, other tin compounds are useful in this way including the other stannous halides. Germanium dichloride and lead dichloride are also useful. Besides palladium-containing complexes, complexes having platinum, rhodium, nickel, and the like may be used in the foregoing way.

Some weak base anion exchange resins are capable of bonding to the metals by both ionic and chemical bonds. The type of exchange reaction which occurs with these metals is therefore a combination of ion and ligand exchange and the resultant complex contains both ionic and chemical bonds between the functional groups of the resin and the metal of the coordination compound.

Among this type of resins are the sulfide resins (containing —SH, or other cationic forms of —SH, such as —SNa, or —SR groups where R is an alkyl or aryl or related group), resins containing pendant cyclopentadienyl anionic groups such as —$C_5H_8Na$, and resins containing pendant allyl groups,

The cyclopentadienyl and allyl groups bond to the metal atom ionically by their charge and chemically by the pi-electrons of the carbon-carbon double bond.

The insoluble resin-metal compound complexes may also be converted to still other materials useful as catalysts by additional steps of oxidation or reduction. Thus, the metal may be oxidized to a higher-valent state by treatment of the complex with an oxidizing agent such as oxygen, hydrogen peroxide, permanganate or dichromate, or reduced to a lower-valent state by treatment of the complex with a reducing agent such as hydrazine, formaldehyde, hypophosphite or an alcohol. Preferably a gaseous reducing agent is used to simplify purification of the resulting catalyst material. Also, the metal compound moiety of the complex may be reduced to zerovalent metal by means of such reducing agents; depending on the catalyst complex subjected to this step, the resulting material may have the zero-valent metal disposed as a shell about the resin particle or completely penetrating the same. The resulting catalyst materials are of particular value for catalyzing hydrogenation and other reactions.

Other useful catalyst materials, comprising modifications of the described complexes, may be made by first treating the starting weak base anion resin containing a functional group with an appropriate reagent to introduce thereto one or more additional functional groups, such as amine, carboxyl, phosphine, sulfur-containing, arsine, or stibine groups. For example, a weak base anion resin containing a primary amine group may be treated with chloro-acetic acid in order to introduce additional carboxyl groups so as to contain iminodiacetic acid groups:

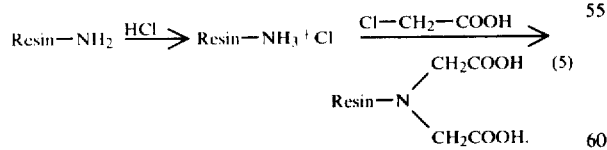

This modified resin contains both amine and carboxyl groups.

A resin originally containing phosphine functional groups may be sulfonated to provide a resin which contains both phosphine and sulfonate groups. The sulfonate groups may be reduced to a sulfinate group or further to a sulfide group to produce resins which contain both phosphine and sulfinate groups or both phosphine and sulfide groups.

The invention may be illustrated by the following examples.

EXAMPLE 1

An insoluble resin-metal compound complex was prepared by suspending about 38.4 grams (g.) of ball-milled Amberlyst-A21 in 100 milliliters (ml.) of water; and to this was added a solution of 6.3 g. of potassium tetrachloropalladite (II), $K_2PdCl_4$, and 15 g. of potassium chloride, KCl, in 200 ml. of water. The mixture was stirred at room temperature overnight. It was filtered (the filtrate contained 17.2 g. of KCl) and the complex was washed with water, then with ethanol, then with ether, and dried at 110° C. for 2 hours. The functional groups of the resin replaced two coordination positions of the starting $Pd^{+2}$ compound. Analysis of the complex showed that it contained, on a weight basis: 7.17% of Pd, 0.06% of K, and 5.34% of Cl.

EXAMPLE 2

Using the complex of Example 1 as a catalyst, allyl chloride, $CH_2$=CH—$CH_2Cl$, was reacted with carbon monoxide (CO) in a CO-insertion reaction. A 300-ml. stirred autoclave was used for the reaction, and into it were placed 5 g. of catalyst, 100 ml. of allyl chloride, and enough carbon monoxide gas to give a total pressure of 1200 pounds per square inch gage (psig). The temperature was held at 250° F. The reaction was run overnight, during which time the pressure fell to 860 psig. The products were analyzed by vapor phase chromatography and a substantial amount of but-3-enoyl chloride, $CH_2$=CH—$CH_2$—COCl, was identified.

EXAMPLE 3

A complex was prepared by dissolving 2 g. of rhodium trichloride trihydrate, $RhCl_3.3H_2O$, in 100 ml. of absolute ethanol, heating to 50° C., and then adding thereto 16 g. of powdered Amberlyst-A21 resin previously moistened with absolute ethanol. The mixture was stirred for about an hour and warmed until most of the color had disappeared, after which it was filtered and the complex washed with absolute ethanol and dried at 110° C. for 1 hour. Analysis showed the complex to contain, on a weight basis: 5.83% of Rh and 5.33% of Cl.

EXAMPLE 4

The complex of Example 3, in an amount of 0.3 g., was used to catalyze a double bond isomerization reaction involving 20 ml. of 1,5-cyclooctadiene, previously purified by passage through a column of alumina powder. The diolefin and catalyst were stirred together for an hour at room temperature and an aliquot was tested for a reaction product by vapor phase chromatography. None was found and the mixture was then heated to 100° C., and again tested, when 1,3- and 1,4-cyclooctadienes were identified.

EXAMPLE 5

Another complex was made as follows. About 15 g. of dichlorobis(triphenylphosphine)cobalt(II), ($CoCl_2(Ph_3P)_2$), dissolved in chloroform, were added to a suspension of 15 g. of dry powdered Amberlyst-A21 in chloroform, and the mixture was stirred at room temperature for 15 minutes. The mixture was filtered and the complex dried at 110° C. for 0.5 hour. The complex contained, on a weight basis: 5.52% of Co, 0.02% of P, and 9.80% of Cl.

EXAMPLE 6

The effect of potassium chloride, KCl, on the penetration of $Pd^{+2}$ coordination compound into particles of Amberlyst-A21 resin was noted in two experiments. In the first, a control experiment, 20 g. of the resin particles in the form of beads of 30 to 40 mesh size were suspended in 50 ml. of water and then mixed with 3.41 g. of $K_2PdCl_4$ dissolved in 50 ml. of water. The mixture was refluxed for 16 hours, with stirring, then filtered, and the beads were washed thoroughly with distilled water to substantially completely remove Cl ion. A bead was cut diametrically in half and examined by microscope; it showed a lightly colored palladium-containing outer annular ring adjacent its exterior boundary and radially inwardly thereof a white center. On treatment of the surface so exposed with hydrazine, the ring became black. Measurement showed the ring or annulus to have a width of 70 microns, as against a bead diameter of 500 microns. In the second experiment, 14 g. of the same resin were stirred with 33 ml. of water at 60° C., and to this were added 100 ml. of a saturated solution of KCl containing 2.2 g. of $K_2PdCl_4$ dissolved therein. This mixture was refluxed as the foregoing one, filtered, and the beads washed thoroughly. A bead was cut in half and treated with hydrazine, after which microscopic examination showed the cut surface to be completely black. In terms of radius, in the second case the entire radius of 250 microns was penetrated; in the first case, a radial distance of only 70 microns was penetrated; thus, in the second case the radial penetration was $250/250 \times 100$ or 100%, and in the first case it was only $70/250 \times 100$ or 28%.

In place of KCl, other alkali metal halides, alkaline earth metal halides, especially the chlorides, and ammonium chloride, may be used.

EXAMPLE 7

A vinyl ester interchange reaction was carried out over 1 g. of the complex of Example 1 as catalyst. Vinyl acetate (10 ml.) and propionic acid (50 ml.) were mixed and heated to 50° C. The complex was added, and the reaction followed by taking samples of reaction mixture and analyzing by vapor phase chromatography. Vinyl propionate and acetic acid were identified as reaction products.

EXAMPLE 8

(a) Vinyl acetate was prepared from ethylene, oxygen, and acetic acid. About 15 ml. of the latter were placed in a reactor with 3 g. of a complex made as in Example 1 and containing about 5% of Pd. Ethylene was passed through the reactor at 15 ml./minute and oxygen at 5 ml./minute. The reactor was heated to 110° C. in an oil bath. Effluents were passed into a cold trap, where product collected and from which samples were removed for analysis by vapor phase chromatography. After an overnight run (16 hours), the products were found to contain a large amount of acetaldehyde, a trace of ethylene oxide, a small amount of vinyl acetate, and a large amount of an unknown material.

(b) The same reaction was run again, this time using as catalyst 2.7 g. of the complex of run (a) above that had been treated with aqueous stannous chloride solution, filtered, washed, and dried. The resulting complex was considered to comprise the resin having bonded thereto $Pd^{+2}$—$Sn^{+2}$ moiety. The reaction was run over a period of 185 minutes. Vinyl acetate at a rate of 5 milligrams (mg.)/hour was obtained, together with a trace of an unknown material.

(c) On repeating the run in (b), except that 0.5 g. of sodium acetate was added to the reactor, the vinyl acetate rate increased to 10 mg./hour over a reaction period of 230 minutes. A trace of ethylene oxide and of an unknown material were obtained.

Thus, with tin, the side reactions are reduced.

EXAMPLE 9

An insoluble resin containing benzyldiphenylphosphine functional groups was prepared as follows:

Into a glass reaction vessel equipped with a high speed stirrer were placed 250 ml. of spectro grade para-dioxan and 8.5 g. of sodium metal. The apparatus was flushed with nitrogen and all of the subsequent procedures were conducted under an atmosphere of nitrogen.

The reaction mixture was heated to the reflux temperature to melt the sodium which was dispersed by the high speed stirrer. The resultant sodium dispersion was then cooled to room temperature and to it were added 10 ml. of a solution composed of 37.2 g. of chlorodiphenylphosphine dissolved in 50 ml. of para-dioxan. The resultant mixture was heated to the reflux temperature and 0.5 g. of naphthalene was added. The remainder of the chlorodiphenylphosphine solution was added to the reaction mixture dropwise over a period of three hours and the final reaction mixture was maintained at the reaction temperature for an additional 16 hours. The solution was cooled at 60° C. and a 50 ml. aliquot of the reaction solution was withdrawn. To the remaining reaction mixture was added 50 g. of a solid resin, the resin being a copolymer of styrene and divinylbenzene which contained chloromethyl functional groups. On addition of the copolymer the reaction mixture temperature rose to 68° C. Additional heat was applied to obtain reflux of the reaction mixture and this temperature was maintained for six hours. The reaction mixture was then allowed to cool to room temperature and was allowed to stand overnight. The solids were then removed by filtration and washed consecutively with methanol, water, methanol, chloroform, benzene, and ether. The resin was then dried in a rotary evaporator at 50° C. The yield of dry solids was 60.8 g. and they were found to have the following chemical analysis, on a weight basis: 3.86% of phosphorus, 13.4% of chlorine, 75.65% of carbon, and 6.19% of hydrogen.

EXAMPLE 10

A complex was prepared by dissolving 40 g. of nickel chloride hexahydrate, $NiCl_2.6H_2O$, in 1 liter (l.) of acetic acid and 1.5 l. of 1-butanol. The solution was heated to the reflux temperature and to this solution were added 20 g. of the phosphine resin of Example 9. The reaction mixture was stirred and maintained at the reflux temperature for 90 minutes. The complex was isolated by filtration, washed with 1-butanol, washed with methanol, washed with ether, and dried in a rotary evaporator. The yield of complex was 21.3 g. and had a chemical analysis, on a weight basis: 0.44% of Ni, 8.45% of Cl, 3.68% of P, 76.73% of C, and 7.53% of H.

EXAMPLE 11

The complex of Example 10 was used as catalyst in a polymerization reaction. An autoclave was charged with 5 g. of complex, 100 ml. of t-butyl alcohol, and 50 ml. of 1,3-butadiene. The contents of the autoclave were heated to 100° C. and pressurized to 770 psig with hydrogen. After 16 hours the pressure had dropped to 440 psig. Hydrogen was again added to bring the pressure to 800 psig and carbon monoxide was added to increase the pressure to 1010 psig. After 7½ hours the pressure had dropped to 943 psig. The reaction mixture was cooled and on opening the autoclave about 1.5 g. of a clear rubbery solid polymer were observed to have been produced. Low molecular weight butadiene oligomers were also produced.

EXAMPLE 12

A complex was prepared by dissolving 1.5 g. of bis-benzonitrile-palladium dichloride in 500 ml. of chloroform and adding to this solution about 20 g. of the phosphine resin of Example 9. The reaction mixture was heated to the reflux temperature for 1 hour at which time 50 ml. of benzonitrile were added and reflux maintained for an additional hour. The reaction mixture was then cooled to room temperature. The complex was isolated by filtration, washed with chloroform and dried in a rotary evaporator. The yield of complex was 21.9 g. and had a chemical analysis, on a weight basis: 1.53% of Pd, 11.2% of Cl, 3.9% of P, 70.02% of C, and 5.84% of H.

EXAMPLE 13

The complex of Example 12 was used in a carbonylation reaction. An autoclave was charged with 5.1 g. of catalyst, 150 ml. of 1-propanol, 1 ml. of concentrated hydrochloric acid, and 25 ml. of liquid propylene. The reaction mixture was stirred, heated to 100° C. and pressurized to 1000 psig with carbon monoxide. The temperature was maintained between 100° and 105° C. After 4 hours the pressure was observed to have decreased to 878 psig. An aliquot of this reaction mixture was then withdrawn and analyzed by vapor phase chromatography and substantial amounts of propyl-n-butyrate and propyl isobutyrate were identified.

EXAMPLE 14

A complex was prepared by dissolving 1.15 g. of tris-triphenylphosphine-rhodium(I) chloride in 75 ml. of ethanol and adding to this solution 3.0 g. of the phosphine resin of Example 9. The mixture was heated to the reflux temperature for three hours and then cooled to room temperature. The complex was isolated by filtration, washed with ethanol, washed with ether, and dried at 110° C.

EXAMPLE 15

The complex of Example 14 was used as catalyst for a hydroformylation reaction. An autoclave was charged with 1 g. of catalyst and 100 ml. of 1-hexene, heated to 100° C. and pressurized to 500 psig with carbon monoxide and then to 1010 psig with hydrogen. After three hours the pressure had decreased to 990 psig. An aliquot of the reaction mixture was then withdrawn and analyzed by vapor phase chromatography. Substantial amounts of heptanal and 2-methyl-hexanal were identified.

EXAMPLE 16

A complex was prepared as follows: A resin, the resin being a solid, macroreticulate copolymer of styrene and divinylbenzene which contained thiol (—SH) functional groups, was exhaustively exchanged with sodium hydroxide to convert the thiol functional group to the sodium form (—SNa). The resultant material was suspended in a solution containing 7 g. of sodium hexachlororhodate(III) and 2 g. of sodium chloride dissolved in 200 ml. of water.

The reaction mixture was stirred, heated to the reflux temperature for 5 hours and then cooled to room temperature. The complex was isolated by filtration, washed with water, washed with methanol, washed with ether, and dried. The yield of complex was 10.5 g. and had a chemical analysis, on a weight basis: 2.81% of Rh and 12.2% of S, and 0.93% of Cl.

EXAMPLE 17

The complex of Example 16 was used as catalyst in a hydroformylation reaction. An autoclave was charged with 1 g. of the complex and 100 ml. of 1-hexene. The contents of the autoclave were heated to 211° F. and a 50/50 mixture of carbon monoxide and hydrogen was added to achieve a pressure of 1000 psig. An exothermic reaction began and at the end of 13 min. reaction time, the pressure had decreased to 675 psig and the temperature had increased to 261° F. The pressure of the reaction was then held at 850 psig by the continual addition of a 50/50 mixture of carbon monoxide and hydrogen at that pressure. After 3 hours reaction time, the autoclave was cooled and the contents analyzed by vapor phase chromatography. This analysis showed that about 76% of the hexene had been converted to heptanal and 2-methyl hexanal which were present in about equal amounts; 2-ethyl pentanal was also present. It was also found that the unreacted hexene was present as a mixture of all of the hexene isomers. The complex could thus promote olefin isomerization as well as hydroformylation.

EXAMPLE 18

The complex used in Example 17 was recovered, washed with 1-hexene and recharged into an autoclave along with 100 ml. of 1-hexene. Using about the same reaction conditions as those of Example 15, the reaction was allowed to proceed for 5 hours and then the autoclave was cooled. The contents were analyzed by vapor phase chromatography. This analysis showed that about 70% of hexene had been converted to heptanal and 2-methyl hexanal which were present in about equal amounts; 2-ethyl pentanal was also present. The complex was then recovered and analyzed for rhodium content. The analysis was 2.15% of Rh.

The unreacted hexene was found to be a mixture of all of the hexene isomers.

From this reaction, it is clearly evident that the complex retained its catalytic activity during the reaction of Example 17 and was still catalytically active after recovery.

EXAMPLE 19

The complex of Example 3 was used as catalyst in a hydroformylation reaction. An autoclave was charged with 3 g. of the complex and 100 ml. of 1-hexene. The contents of the autoclave were then heated to 100° C. and a 50/50 mixture of carbon monoxide and hydrogen was added to give a pressure of 1000 psig. The pressure was maintained between 200 and 1000 psig by periodic addition of the carbon monoxide-hydrogen mixture. After 90 minutes, a sample of the reaction mixture was withdrawn and analyzed by vapor phase chromatography. This analysis showed that about 70% of the hexene had been converted to a mixture of heptanal and 2-methyl hexanal which were present in the respective ratio of about 3/1. Isomeric hexenes were also identified. Thus, the complex could promote isomerization of olefins as well as hydroformylation.

EXAMPLE 20

The complex of Example 19 was recovered and reused as catalyst for another hydroformylation reaction. The reactants and conditions were identical to those of Example 19. After 2.3 hours a sample of the reaction mixture was withdrawn and analyzed by vapor phase chromatography. This analysis showed that about 30% of the hexene had been converted to a 2.8/1 mixture of heptanal and 2-methyl hexanal. Isomeric hexenes were also identified.

From this reaction, it is clearly evident that the complex retained its catalytic activity during the reaction of Example 19, and was still catalytically active after recovery.

EXAMPLE 21

The complex of Example 20 was recovered and used as catalyst for a hydrogenation reaction. An autoclave was charged with the complex and 100 ml. of 1-hexene. The contents of the autoclave were heated to 208° F. and hydrogen was added to give a pressure of 1000 psig.

The pressure rapidly dropped and the temperature increased to 350° F. Hydrogen was added periodically to maintain a pressure between 175 psig and 1000 psig. After 82 minutes a sample of the reaction mixture was withdrawn and analyzed by vapor phase chromatography. This analysis showed that about 77% of the hexene had been converted to hexane. Isomeric hexenes were also identified.

Examples 22 to 25 will compare the activity of catalysts prepared from strong base anion exchange resins and from weak base anion exchange resins.

EXAMPLE 22

This example illustrates the non-equivalence of strong base and weak base type anion exchange resins in a catalytic reaction.

In this example, two resins were employed. The first resin was a commercial strong base anion exchange resin (Rohm and Haas A-26) which is composed of a porous copolymer of styrene and divinylbenzene containing benzyltrimethylammonium hydroxide functional groups. This material as received was in the chloride form and will be referred to as "$S_2$". The second resin was a commercial weak base anion exchange resin (Rohm and Haas A-21) which is composed of a porous copolymer of styrene and divinylbenzene containing benzyl dimethyl amine functional groups. This material as received was in the free base form and will be referred to as "W".

Five ml. aliquots of each of the above resins, "$S_2$" and "W", were treated identically as pairs to prepare a series of catalysts for comparison. Each was washed chromatographically with about 100 ml. of 1 N aqueous sodium nitrate and then washed five times batchwise with 50 ml. of distilled water.

The two resins, "$S_2$" and "W", were treated identically to incorporate copper as follows:

A 10 ml. portion of 0.1 M $Cu(NO_3)_2$ was added to the wet resin. Contact was continued for 15 min. with occasional stirring. The liquid was decanted at the end of this time. The metal-loaded resin was washed with three 10 ml. portions of distilled water and transferred to a millipore funnel with an additional 10 ml. of water from a wash bottle. It was then dried by pulling air through the funnel for 20 min.

The two resins, "$S_2$" and "W", were treated identically to incorporate nickel using the same procedure described above except that 0.1 M $Ni(NO_3)_2$ was used instead of $Cu(NO_3)_2$.

The two resins, "$S_2$" and "W", were treated identically to incorporate iron using the procedure described above except that 0.1 M $FeSO_4$ was used instead of $Cu(NO_3)_2$.

The catalysts prepared as above were compared for catalytic activity in the decomposition of hydrogen peroxide. In each test 2 ml. of the resin were suspended in 10 ml. of water, and 5 ml. of 30% aqueous hydrogen peroxide were injected into the stirred mixture. Oxygen evolution was then measured in each case for 15 min. The results of these tests are tabulated below.

| Metal | Copper | | Nickel | | Iron | |
|---|---|---|---|---|---|---|
| Resin | $S_2$ | W | $S_2$ | W | $S_2$ | W |
| Oxygen evolution ml./15 min. | 1.6 | 34.5 | 0.4 | 4.2 | 1.0 | 2.0 |

These results clearly show that for this reaction all metals were catalytically more active when incorporated into the weak base anion exchange resin than when incorporated into the strong base anion exchange resin.

EXAMPLE 23

This example will compare the effect of catalysts prepared from strong base and weak base anion exchange resins for hydroformylation.

Two catalysts were prepared in identical treatments, one from a strong base anion exchange resin (a crosslinked copolymer of styrene and divinylbenzene containing benzyltrimethyl ammonium chloride functional groups) designated as "S" and one from a weak base anion exchange resin (a crosslinked copolymer of styrene and divinylbenzene containing benzyldimethyl amine functional groups) designated as "W".

Twenty ml. of each resin were suspended in methanol, transferred to a chromatography column and exchanged with 1 l. of 2 N NaOH to convert the resins to their base form. They were then treated with 1 l. of 2 N NaCl, 1 l. of $H_2O$ and 1 l. of acetone. Twenty ml. of each resin were then contacted in a flask, with stirring, with 50 ml. of an acetone solution containing 100 mg. of tetraethylammonium tricosacarbonyl dodeca rhodate (($C_2H_5$)$_4$N) ($Rh_{12}(CO)_{30}$) for two hrs. at room temperature. At the end of this time all of the rhodium had been incorporated into the resin matrix and each resin contained about 0.5% by weight bound rhodium. These catalysts are designated $S_A$ and $W_A$.

Each resin was tested for catalytic activity and selectivity in an identical reaction, the hydroformylation of 1-hexene, according to the following procedure:

A 300 ml. stirred autoclave was charge with 5 ml. of catalyst and 100 ml. of 90% benzene and 10% methanol as solvent. The autoclave was flushed with carbon monoxide and heated to 100° C. and pressurized to 1000 psig with a 1/1 molar mixture of CO and $H_2$. Twenty ml. of 1-hexene were then injected into the autoclave and the reaction was followed by pressure drop and by periodic sampling. The pressure was maintained between 800 and 1000 psig during the entire test. The results of these tests were as follows.

| Catalyst | $W_A$ | $S_A$ |
|---|---|---|
| Time, min. | 12 | 12 |
| Product Composition %: | | |
| 1-hexene | 61.7 | 97.5 |
| 2(3)-hexenes- | 23.6 | 1.2 |
| branched heptanals | 3.6 | 0.3 |
| linear heptanal | 11.1 | 1.0 |
| % Conversion to Aldehyde | 14.7 | 1.3 |

These data show that the catalyst made from the weak base anion exchange resin was much more active for olefin isomerization and hydroformylation.

EXAMPLE 24

This example will further compare the effect of catalysts prepared from strong base and weak base anion exchange resins in hydroformylation.

Two catalysts were prepared in identical treatments, one from a strong base type anion exchange resin (a crosslinked copolymer of styrene and divinylbenzene containing benzyltrimethyl ammonium chloride functional groups) designated as "S" and one from a weak base anion exchange resin (a crosslinked copolymer of styrene and divinylbenzene containing benzyldimethyl amine functional groups) designated as "W".

Twenty ml. of each resin suspended in water were contacted in a flask, with stirring, with 125 ml. of an aqueous solution containing 0.657 g. of sodium hexachlororhodate ($Na_3RhCl_6.12H_2O$) for 1.5 hrs. at room temperature. The mixtures were then heated to reflux for 0.5 hr. and cooled. At this point all of the rhodium had been incorporated into the resin matrices. These catalysts are designated $S_B$ and $W_B$. $S_B$ contained 1.7% Rh; $W_B$ contained 1.9% Rh.

Each resin ($S_B$ and $W_B$) was tested for catalytic activity and selectivity in an identical reaction, the hydroformylation of 1-hexene, according to the following procedure.

A 300 ml. stirred autoclave was charged with 5 ml. of catalyst and 100 ml. of 90% benzene and 10% methanol as solvent. The autoclave was flushed with carbon monoxide and heated to 90° C. and pressurized to 1000 psig with a 1/1 molar mixture of CO and $H_2$. Twenty ml. of 1-hexene were then injected into the autoclave and the reaction was followed by pressure drop and by periodic sampling. The pressure was maintained between 800 and 1000 psig during the entire test. The results of these tests were as follows:

| Catalyst | $W_B$ | $S_B$ |
|---|---|---|
| Time, Min. | 90 | 90 |
| Product Composition %: | | |
| 1-hexene | 0 | 100 |
| 2(3)-hexenes | 42.4 | 0 |
| branched heptanals | 17.4 | 0 |
| linear heptanal | 34.8 | 0 |
| branched heptanols | 1.3 | 0 |
| linear heptanol | 4.1 | 0 |
| conversion of olefin | 57.6 | 0 |

These data show that the catalyst made from the weak base anion exchange resin was effective for olefin isomerization and hydroformylation and for aldehyde reduction to alcohol; the catalyst made from the strong base anion exchange resin showed no activity.

EXAMPLE 25

This example will compare the effect of catalysts prepared from strong base and weak base anion exchange resins.

Two catalysts were prepared in identical treatments, one from a strong base type anion exchange resin (a crosslinked copolymer of styrene and 15% divinylbenzene containing tributylphenylphosphonium bromide functional groups) designated as "$S_I$" and one from a weak base anion exchange resin (a crosslinked copolymer of styrene and 15% divinylbenzene containing dibutylphenylphosphine functional groups) designated as "$W_I$".

A 10 g. portion of each resin was suspended in 25 ml. of 95% ethanol/5% water solvent and contacted in a flask, with stirring, with 100 ml. of a solution of the same solvent system containing 0.27 g. of chloroplatinic acid ($H_2PtCl_6.6H_2O$) and 0.83 g. of stannous chloride ($SnCl_2.2H_2O$). This system was then heated to reflux for 2.5 hrs., 2.8 ml. of concentrated hydrochloric acid were added and the reflux was continued for 20 min. more. A stream of hydrogen gas at about 150 ml/min. was passed through the solution as the refluxing was continued for a final 1 hr. The catalysts were then washed extensively with anhydrous methanol and each stirred for 0.5 hr. in a mixture consisting of 10 ml. of water, 38 ml. of anhydrous methanol, and 57 ml. of 0.1 M aqueous sodium hydroxide saturated with sodium chloride. Each was then filtered off, washed with five 100 ml. portions of water, then five 100 ml. portions of anhydrous methanol, and then stored as a suspension in anhydrous methanol until use.

Each of the above resins containing platinum and tin was tested for catalytic activity and selectivity in an identical reaction, the hydrogenation of 1,5-hexadiene, according to the following procedure:

A 300 ml. stirred autoclave was charged with the methanol-suspended catalyst (a total of 27 ml. of resin and solvent) and 60 ml. of 40% anhydrous methanol, 60% xylene by volume as solvent. The autoclave was flushed with hydrogen, heated to 70° C. and pressurized to 1000 psig with hydrogen. Twenty ml. of 1,5-hexadiene were then injected into the autoclave and the reaction was followed by pressure drop and by periodic sampling. The pressure was maintained between 800 and 1000 psig during the entire test. The results at comparable conversions show that the catalyst from the weak base resin was much more selective for olefin formations vs. paraffin formation.

| Catalyst from resin | $W_I$ | $S_I$ |
|---|---|---|
| Product Composition, %: | | |
| n-hexane | 32.3 | 55.6 |
| 1-hexene | 44.4 | 20.3 |
| 2(3)-hexenes | 2.4 | 0 |
| 1,5-hexadiene | 19.5 | 24.1 |
| other dienes | 1.4 | 0 |
| % Conversion of diene | 79.1 | 75.9 |
| Olefin/Paraffin Ratio | 1.45 | 0.37 |

What is claimed is:

1. In a method of carrying out a metal-compound catalyzed reaction, the improvement comprising employing as a catalyst an insoluble resin-metal coordinative complex compound comprising an insoluble weak base anion exchange resin having amine, phosphine, arsine, stibine, thiol or sulfide Lewis base substituents, said resin being coordinatively, nonionically bonded through said substituent to a metal atom selected from the group consisting of platinum, palladium, rhodium, ruthenium, osmium, iridium, gold, cadmium, titanium, zirconium, hafnium, vanadium, chromium, molybdenum, tungsten, manganese, rhenium, iron, cobalt, nickel, copper, zinc, silver, and mercury.

2. The method of claim 1 wherein said metal atom of said complex has chemically bonded thereto at least one ligand.

3. The method of claim 1 wherein said complex contains on a weight basis 0.01 to 50% of metal, 0 to 60% of ligand, and 39 to 99% of resin.

4. The method of claim 1 wherein said metal atom of said complex has chemically bonded thereto a tin-containing moiety of a stannous halide.

5. The method of claim 1 wherein said metal-compound catalyzed reaction is the hydrogenation of an olefin.

6. The method of claim 5 wherein said metal-compound catalyzed reaction is the hydrogenation of an olefin and said chemically bonded metal atom is platinum.

7. The method of claim 5 wherein said olefin is a diene.

8. The method of claim 6 wherein said olefin is a diene.

9. The method of claim 1 wherein said metal-compound catalyzed reaction is the selective hydrogenation of diolefins.

10. The method of claim 1 wherein said metal-compound catalyzed reaction is a carbon monoxide insertion reaction.

* * * * *